(12) United States Patent
Fumagalli

(10) Patent No.: US 11,096,635 B2
(45) Date of Patent: Aug. 24, 2021

(54) SYSTEM FOR CONTROLLING AT LEAST ONE MOVEMENT OF A MOTORIZED COMPONENT OF RADIOLOGICAL EQUIPMENT THAT USES IT

(71) Applicant: GENERAL MEDICAL MERATE S.P.A., Seriate (IT)

(72) Inventor: Mauro Fumagalli, Seriate (IT)

(73) Assignee: GENERAL MEDICAL MERATE S.P.A., Seriate (IT)

( * ) Notice: Subject to any disclaimer, the term of this patent is extended or adjusted under 35 U.S.C. 154(b) by 1 day.

(21) Appl. No.: 16/753,901

(22) PCT Filed: Oct. 10, 2018

(86) PCT No.: PCT/IB2018/057849
§ 371 (c)(1),
(2) Date: Apr. 6, 2020

(87) PCT Pub. No.: WO2019/073406
PCT Pub. Date: Apr. 18, 2019

(65) Prior Publication Data
US 2020/0261037 A1 Aug. 20, 2020

(30) Foreign Application Priority Data
Oct. 11, 2017 (IT) .......................... 102017000114495

(51) Int. Cl.
*A61B 6/10* (2006.01)
*A61B 6/04* (2006.01)
*A61B 6/00* (2006.01)

(52) U.S. Cl.
CPC ............ *A61B 6/102* (2013.01); *A61B 6/0487* (2020.08); *A61B 6/467* (2013.01); *A61B 6/54* (2013.01)

(58) Field of Classification Search
CPC ...... H04W 24/00; H04W 24/03; G06N 20/00; G06F 3/011; G06F 3/01; G06F 3/017;
(Continued)

(56) References Cited

U.S. PATENT DOCUMENTS 3,803,417 A 4/1974 Kok
2015/0085986 A1 3/2015 Dinse et al.
(Continued)

FOREIGN PATENT DOCUMENTS

JP H11285492 A 10/1999

*Primary Examiner* — Don K Wong
(74) *Attorney, Agent, or Firm* — Dickinson Wright PLLC; Andrew D. Dorisio

(57) ABSTRACT

A system for controlling a motorised component of radiological equipment using a device with a control lever having a first end constrained to a base manoeuvred by gripping a handle with a hand. First and second electric sensors are associated with a grip of the control lever. The first electric sensor is located at a first point of the grip and adapted to detect the presence of a finger. The second electric sensor is located at a second point of the handle of the control lever and adapted to detect the presence of a finger at the second point. Another electric sensor is for detecting the positioning of the control lever with respect to the base. An electronic unit is connected to the electric sensors for causing movement as a function of the positioning of the control lever only if the first and/or second electric sensors detect a presence.

12 Claims, 2 Drawing Sheets

Figure 1:
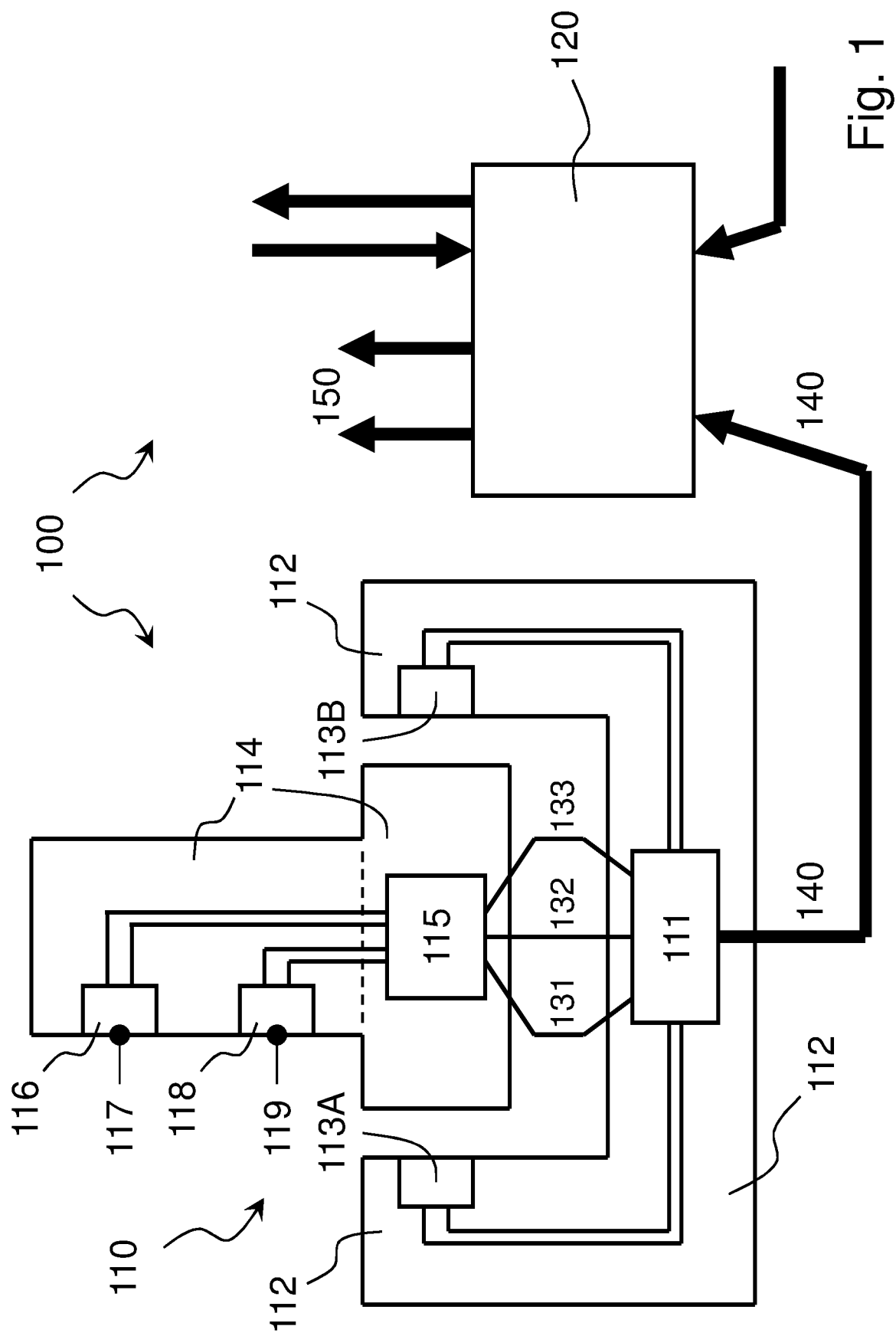

(58) Field of Classification Search
CPC ... G06F 3/02; G06F 3/03; A61B 6/102; A61B 6/54; A61B 6/467
See application file for complete search history.

(56) References Cited

U.S. PATENT DOCUMENTS

2017/0128030 A1    5/2017   Kong et al.
2019/0102927 A1*   4/2019   Yokokawa .............. G06F 3/014

* cited by examiner

SYSTEM FOR CONTROLLING AT LEAST ONE MOVEMENT OF A MOTORIZED COMPONENT OF RADIOLOGICAL EQUIPMENT THAT USES IT

FIELD OF THE INVENTION

The present invention relates to a system for controlling at least one movement of a motorised component of radiological equipment and radiological equipment that uses it.

BACKGROUND

Modern radiological equipment has various motorised components that interact with patients and/or operators and/or the environment (e.g. the patient table, the head with the radiogenic tube, the support column, etc.) and is provided with a system for controlling the movements of the motorised components.

One of the solutions adopted in such control systems is the so-called "joystick", i.e. a lever having an end that is constrained to a base and adapted to be manoeuvred by an operator typically at the other end; the movement of a component is a function of the positioning of the lever.

It may happen that the lever is accidentally manoeuvred by an operator or that the lever is moved accidentally by an object. In these cases, the component also moves even if there is no need or desire of an operator.

There is a risk that this movement could cause damage to the equipment and/or to the patient.

As known, radiological equipment presents other risks. For years, the most strongly felt need is that connected with the accidental emission (i.e. not desired by the operator) of X-rays. Such risk is tackled for example by the solution described and illustrated in the US patent application published under no. 2017/128030 A1.

SUMMARY

The general aim of the present invention is to improve existing radiological equipment from a safety point of view.

Such objective is substantially reached thanks to what is expressed in the appended claims that form an integral part of the present description.

The idea underpinning the present invention is to associate at least two electric sensors, in particular two capacitive sensors, with the control lever of the movement of one or more motorised components, adapted to enable/disable the movement. As can be understood from the following detailed description, various strategies can be adopted based on the detections of the two sensors to reduce the risk of accidental movements.

According to an advantageous embodiment, the control system comprises a device with a control lever having a first end constrained to a base so as to allow at least its inclination with respect to the base and being adapted to be manoeuvred by an operator by gripping a handle thereof; at least a first electric sensor and a second electric sensor are associated with the handle of the control lever; the first electric sensor is located at a first point of the handle of the control lever and is adapted to detect the presence of at least one finger of the operator's hand at the first point; the second electric sensor is located at a second point of the handle of the control lever and is adapted to detect the presence of at least one finger of the operator's hand at the second point; at least one other electric sensor is associated with the base and is adapted to detect the positioning of the control lever, in particular the degree of inclination and possibly the inclination direction, with respect to the base; the control system further comprises an electronic unit electrically connected to the electric sensors and adapted to cause movement as a function of the positioning of the control lever only if the first electric sensor is detecting a presence (typically, the presence of at least one finger of the operator's hand) and/or only the second electric sensor is detecting a presence (typically, the presence of at least one finger of the operator's hand).

LIST OF FIGURES

Figure 2:
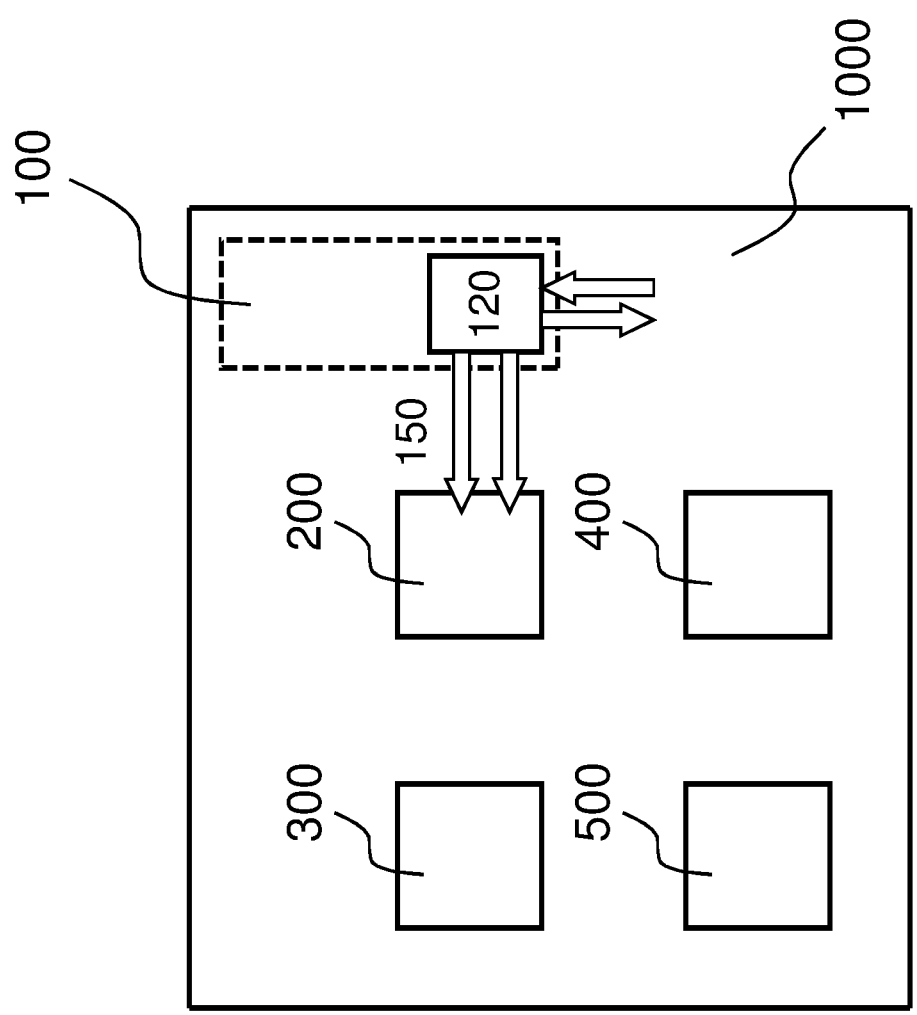

The present invention will become clearer from the following detailed description to be considered together with the appended drawings in which:

FIG. 1 very schematically shows an embodiment of a control system according to the present invention, and FIG. 2 shows a general block diagram of radiological equipment according to the present invention.

As can be easily understood, there are various ways of practically implementing the present invention which is defined in its main advantageous aspects in the appended claims.

DETAILED DESCRIPTION

FIG. 1 very schematically shows an embodiment of a control system 100 according to the present invention; it is substantially divided into a control device 110 and an electronic unit 120, connected electrically to each other by an electrical cable 140. In general, the system 100 can comprise various control devices that are identical or similar to the device 110 electrically connected to the unit 120.

In general, the electronic unit 120, which is typically of the computerised type, is adapted to perform other operations as well as those performed in cooperation with the device 110; therefore, the unit 120 can be considered part of a control system according to the present invention, but also part of other systems. For this reason, in FIG. 2, the system 100 has been represented as a rectangle in a broken line inside which the unit 120 is placed.

FIG. 2 shows a general block diagram of radiological equipment 1000 according to the present invention; there is a control system 100, a motorised component 200 (in general there will be others) and, for example, other components 300, 400 and 500 of the radiological equipment 1000. From the unit 120 for example two electrical cables exit which then enter into the motorised component 200; these cables transfer electrical movement driving signals. Then there are other cables that enter and exit from the unit 120 for performing other operations.

The device 110 comprises a fixed base 112 and a movable control lever 114; the lever 114 has a first end constrained to the base 112 and adapted to be manoeuvred by an operator's hand, in particular through a grip thereof, by varying its inclination. According to the example of FIG. 1, at the first end the lever 114 has an element, in particular an enlargement (e.g. imprisoned in a seat of the base 112), which allows at least the lever 114 to be rotated (which can be referred to as a "two-dimensional hinge").

According to the example of FIG. 1, a broken line divides the enlargement and the handle that are adjacent and joined directly; alternatively, these two elements may be configured differently and/or spaced and joined through another element. In any case, the handle extends along one direction and can be conceptually divided into three zones: a first end zone near the base, a second end zone far from the base and a third intermediate zone between the first zone and the second zone.

There is a first electric sensor 116 and a second electric sensor 118 associated with the lever 114, precisely with the handle; the first electric sensor 116 is located at a first point 117 of the lever 114 (precisely of the handle), e.g. in the second zone or in the third zone, and is adapted to detect the presence of at least one finger of the hand of the operator who grips the handle at the first point 117; the second electric sensor 118 is located at a second point 119 of the lever 114 (precisely of the handle), e.g. in the third zone or in the first zone, and is adapted to detect the presence of at least one finger of the hand of the operator who grips the handle at the second point 119. The distance between the second point 119 and the base 112 (in the extension direction of the handle of the lever 114) is less than the distance between the first point 117 and the base 112 (in the extension direction of the handle of the lever 114).

It is to be noted that the electric sensors on the grip of the control system according to the present invention are designed to detect the presence of a part of a human body; therefore, being positioned on a handle, they typically detect the presence of a finger or of two fingers of a hand; however, they can come into contact with other parts of a human body (e.g. of a hand or of an arm) and detect such presence. There is at least one other electric sensor associated with the base 112 and adapted to detect the positioning of the lever 114—this is known in the "joystick" sector therefore no details will be provided (in general, the lever of a joystick can be inclined in any direction, it can be turned about an axis thereof and can be slightly translated along an axis thereof; it can further be provided with one or more buttons); in FIG. 1, for example, another two electric sensors 113A and 113B are shown, for detecting any inclination of the lever.

The expression "electric sensor" means, according to usual technical terminology, an electrical component that is free from moving mechanical parts and therefore that does not correspond to an electric button, to an electric switch or to an electric microswitch.

The electronics can be subdivided, for example and advantageously, into three parts: into the lever 114 (circuitry 115), the base 112 (circuitry 111) and the electronic unit 120.

The sensor 116 is electrically connected to the circuitry 115 for example through two electrical conductors; the sensor 118 is electrically connected to the circuitry 115 for example through two electrical conductors; the sensor 113A is electrically connected to the circuitry 111 for example through two electrical conductors; the sensor 113B is electrically connected to the circuitry 111 for example through two electrical conductors; the circuitry 115 is connected to the circuitry 111 for example and advantageously through three electrical conductors (alternatively there could be two or four): a first conductor 131, a second conductor 132, and a third conductor 133;

the circuitry 111 is connected to the unit 120 through an electrical cable 140 formed by a certain number of conductors.

The electrical signals deriving from the detections of the sensors 116 and 118 are received at the circuitry 115 that processes them and sends them to the circuitry 111. The electrical signals deriving from the detections of the sensors 113A and 113B are received at the circuitry 111 that processes them. The circuitry 111 sends the signals processed by the sensors 116, 118, 113A and 113B to the electronic unit 120. The electronic unit 120 is adapted, amongst other things, to cause movements of the component 200 based on the signals received from the circuitry 115 (consequence of the detections performed by the sensors 116, 118, 113A and 113B) and, in particular as a function of the positioning of the lever 114.

According to an alternative embodiment, there is no electronic circuitry in the control lever, i.e. the electronics are subdivided into two parts instead of into three parts. In this case, the functions of the circuitry 115 and of the circuitry 111 will be performed by a single circuitry in the base 112.

According to the present invention, in general, the electronic unit 120 is adapted to cause one (or more) movements as a function of the positioning of the lever 114, precisely its degree of inclination and possibly its inclination direction, only if the sensor 116 on the handle is detecting a presence (typically the presence of a finger of the hand that grips the handle of the lever 114) and/or the sensor 118 on the handle is detecting a presence (typically the presence of a finger of the hand that grips the handle of the lever 114).

Thanks to the double sensor on the handle, accidental movements of a component of radiological equipment can be prevented. As can be understood below, various strategies can be adopted based on the detections of the double sensor to reduce the risk of accidental movements. In any case, the choice to use the grip of the control lever of electric sensors, in particular capacitive sensors, rather than buttons or switches, reduces such risk; in fact, the contact of many objects with the sensor can be distinguished from the contact of a finger with the sensor.

According to a first possibility, the movement is simply subject to a detection by part of any one of the two sensors.

According to a second possibility, the movement is subject to a detection by only one of the two sensors which is at an end zone of the handle of the control lever; this solution is advantageous if it is considered possible that the other sensor signals a detection, but the operator has not voluntarily initiated such detection.

According to a third possibility, the movement is subject to a detection by only one of the two sensors which is at an intermediate zone of the handle of the control lever; this solution is advantageous if it is considered possible that the other sensor signals a detection, but the operator has not voluntarily initiated such detection.

According to a fourth possibility, the movement is subject to a detection both by a first of the two sensors (e.g. the sensor 116) and by a second of the two sensors (e.g. sensor 118); this solution is very safe as it is very unlikely that an operator or an object involuntarily touches both sensors and involuntarily tilts the lever.

According to a fifth possibility, the electronic unit 120 is adapted to cause movement as a function of the positioning of the lever 114:
  at a first speed if the sensor 116 is detecting a presence (in particular of a finger) or if the sensor 118 is detecting a presence (in particular of a finger);
  at a second speed if the sensor 116 is detecting a presence (in particular of a finger) and the sensor 118 is detecting a presence (in particular of a finger);
preferably, the second speed is higher than the first speed.

In this way, any accidental activations cause movements at reduced speed, therefore less dangerous.

The sensors in the control lever are preferably of the capacitive type.

The number of sensors in the control lever may also be more than two; however, the use of two sensors is a good compromise between safety and simplicity.

The positioning of the sensors on the control lever is chosen according to the lever and the application. The positioning shown in FIG. 1 is only indicative.

According to the embodiment of the present invention, the electrical signals processed by the various electronic circuits may be of the analog and/or digital type. Typically, the electrical signals that exit from the electric sensors (indicated with 116, 118, 113A and 113B in FIG. 1) are of the analog type.

According to the embodiment of the present invention, the signals that exit from the circuitry 115 may be of the analog or digital type.

According to the embodiment of the present invention, the signals that exit from the circuitry 111, i.e. from the device 110, may all be of the analog type or all of the digital type or some of the analog and some of the digital type.

The lever 114, in particular its circuitry 115, is electrically connected to the base 112, in particular to its circuitry 111, through a limited number of electrical conductors, preferably two or three; this is advantageous for facilitating the movement of the lever 114 with respect to the base 112.

There may only be two of these conductors; in this case the circuitry 115 must be able to superpose the detections of the sensors with the power supply coming from the circuitry 111.

There may be three of these conductors (as shown in FIG. 1); in this case, a first electrical conductor 131 is used to transmit the ground voltage, a second electrical conductor 132 is used to transmit the supply voltage, a third electrical conductor 133 is used to transmit detections of the sensors 116 and 118.

If three electrical conductors and signals of the analog type are used for the connection between the circuitry 115 and the circuitry 111, it is advantageous that:
- a first analog level indicates that no electric sensor is detecting a presence (in particular of a finger), preferably corresponding to the supply voltage;
- a second analog level indicates that only the sensor 116 is detecting a presence (in particular of a finger);
- a third analog level indicates that only the sensor 118 is detecting a presence (in particular of a finger);
- a fourth analog level indicates that both the sensor 116 is detecting a presence (in particular of a finger) and the sensor 118 is detecting a presence (in particular of a finger);
- a fifth analog level indicates a malfunctioning condition of the device 110 (in particular of the lever 114), preferably corresponding to ground voltage.

The invention claimed is:

1. System for controlling at least one movement of a component of radiological equipment, said component being motorised and adapted to interact with patients or operators or the environment, the system comprising a device with a control lever having a first end constrained to a base so as to allow at least its inclination with respect to the base and being adapted to be manoeuvred by an operator by gripping a handle thereof with a hand;
    wherein at least one first electric sensor and one second electric sensor are associated with said handle of said control lever;
    wherein said first electric sensor is located at a first point of said handle of said control lever and is adapted to detect a first presence of at least one finger of said hand at said first point;
    wherein said second electric sensor is located at a second point of said handle of said control lever and is adapted to detect a second presence of at least one finger of said hand at said second point;
    wherein at least another electric sensor is associated with said base and is adapted to detect the positioning of said control lever, in particular the degree of inclination or the direction of inclination, with respect to said base;
    further comprising an electronic unit electrically connected to the electric sensors;
    wherein said electronic unit is adapted to cause said movement as a function of the positioning of said control lever only if said first electric sensor is detecting the first presence or only if said second electric sensor is detecting the second presence.

2. System according to claim 1, wherein said first point is located in a first zone of said handle of said lever and said second point is located in a second zone of said handle of said lever, said first zone being distant from said second zone, wherein said electronic unit is adapted to cause said movement as a function of the positioning of said control lever and as a function of the positions or of the distance of said first zone and said second zone.

3. System according to claim 1, wherein said electronic unit is adapted to cause said movement as a function of the positioning of said control lever:
    at a first speed if said first electric sensor is detecting the first presence or said second electric sensor is detecting the second presence;
    at a second speed if said first electric sensor is detecting the first presence and said second electric sensor is detecting the second presence;
said second speed being greater than said first speed.

4. System according to claim 1, wherein said electronic unit and said device are adapted to exchange electrical signals of a digital type to transmit detections of said electric sensors, in particular of said first electric sensor and said second electric sensor.

5. System according to claim 1, wherein said electronic unit and said device are adapted to exchange electrical signals of an analog type to transmit detections of said electric sensors, in particular of said first electric sensor and said second electric sensor.

6. System according to claim 4, wherein only two electrical conductors connect said control lever to said base.

7. System according to claim 4, wherein only three electrical conductors connect said control lever to said base, a first electrical conductor serves to transmit the ground voltage, a second electrical conductor serves to transmit the supply voltage, a third electrical conductor serves to transmit detections of said first electric sensor and said second electric sensor.

8. System according to claim 7, wherein:
    a first analog level indicates that no electric sensor is detecting any presence;
    a second analog level indicates that only said first electric sensor is detecting the first presence;
    a third analog level indicates that only said second electric sensor is detecting the second presence;
    a fourth analog level indicates that both said first electric sensor is detecting the first presence and said second electric sensor is detecting the second presence;
    a fifth analog level indicates a malfunctioning condition of said device.

9. System according to claim 1, comprising two or more control devices.

10. Radiological equipment comprising a control system according to claim 1.

11. Radiological equipment according to claim 10, wherein said base is fixed or integrated into a control console.

12. Radiological equipment according to claim 10, wherein said electronic unit is of the computerised type and is adapted to perform other operations in the equipment.

* * * * *